United States Patent
Biel

(10) Patent No.: US 6,471,396 B2
(45) Date of Patent: Oct. 29, 2002

(54) METHOD AND APPARATUS FOR DETECTING THE PRESENCE OF A MOULDING IN AN OPEN BLISTER PACKAGE BASED ON SENSED TEMPERATURE DIFFERENCES

(75) Inventor: Roger Biel, Frankfurt am Main (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/725,405

(22) Filed: Nov. 29, 2000

(65) Prior Publication Data

US 2001/0009561 A1 Jul. 26, 2001

(30) Foreign Application Priority Data

Dec. 3, 1999 (DE) .......................... 99124220

(51) Int. Cl.[7] .................. G01N 25/72; G01N 21/88; G01N 21/95
(52) U.S. Cl. ................. 374/45; 374/4; 374/124; 374/129; 250/358.1
(58) Field of Search .................. 374/45, 4, 5, 6, 374/7, 120, 121, 124, 129, 53, 16, 10; 250/358.1, 340, 342, 338.1; 53/52, 55, 56, 57, 58, 493, 494, 498

(56) References Cited

U.S. PATENT DOCUMENTS

| | | | | |
|---|---|---|---|---|
| 4,245,243 A | * | 1/1981 | Gutjahr et al. ............. | 348/92 |
| 5,433,106 A | * | 7/1995 | Matsumura et al. ........ | 374/124 |
| 5,555,707 A | * | 9/1996 | Schwenger .................. | 53/493 |
| 5,568,715 A | * | 10/1996 | Ebel et al. .................... | 53/494 |
| 5,730,526 A | * | 3/1998 | Davis et al. .................. | 374/45 |
| 5,775,806 A | * | 7/1998 | Allred ............................ | 374/5 |
| 5,799,468 A | * | 9/1998 | Eck et al. ..................... | 53/237 |
| 5,823,677 A | * | 10/1998 | Forester et al. ............... | 374/10 |
| 6,124,594 A | * | 9/2000 | Duggan et al. .......... | 250/341.8 |
| 6,246,062 B1 | * | 6/2001 | Ross et al. ............... | 250/461.1 |

FOREIGN PATENT DOCUMENTS

| | | | | |
|---|---|---|---|---|
| DE | 43 31 772 A1 | | 3/1995 | |
| DE | 196 29 101 A 1 | | 1/1998 | |
| DE | 298 22 017 U 1 | | 5/1999 | |
| EP | 0252453 | * | 1/1988 | ............ 374/4 |
| EP | 0 567 078 A2 | | 10/1993 | |
| EP | 0 691 273 A1 | | 1/1996 | |
| FR | 2651322 | * | 3/1991 | ............ 374/45 |
| GB | 2309 077 A | | 7/1997 | |
| JP | 63-191932 | * | 8/1988 | ............ 374/45 |

\* cited by examiner

Primary Examiner—Diego Gutierrez
Assistant Examiner—Stanley J. Pruchnic, Jr.
(74) Attorney, Agent, or Firm—R. Scott Meece; Jian S. Zhou; Richard I. Gearhart

(57) ABSTRACT

The invention relates to a method and a device for registering the presence of an ophthalmic moulding consisting of a biocompatible polymeric material, especially an ophthalmic lens, particularly a contact lens, in a package. The invention solves the problem through the use of an IR camera. Packages containing a moulding, especially a contact lens, have a change in their temperature distribution compared with a package without a contact lens. By evaluating the temperature difference, it is possible to determine whether or not there is a contact lens in a package. In particular, by using the detecting method according to the invention, one can determine whether there is a contact lens in the package directly after the filling procedure.

20 Claims, 2 Drawing Sheets

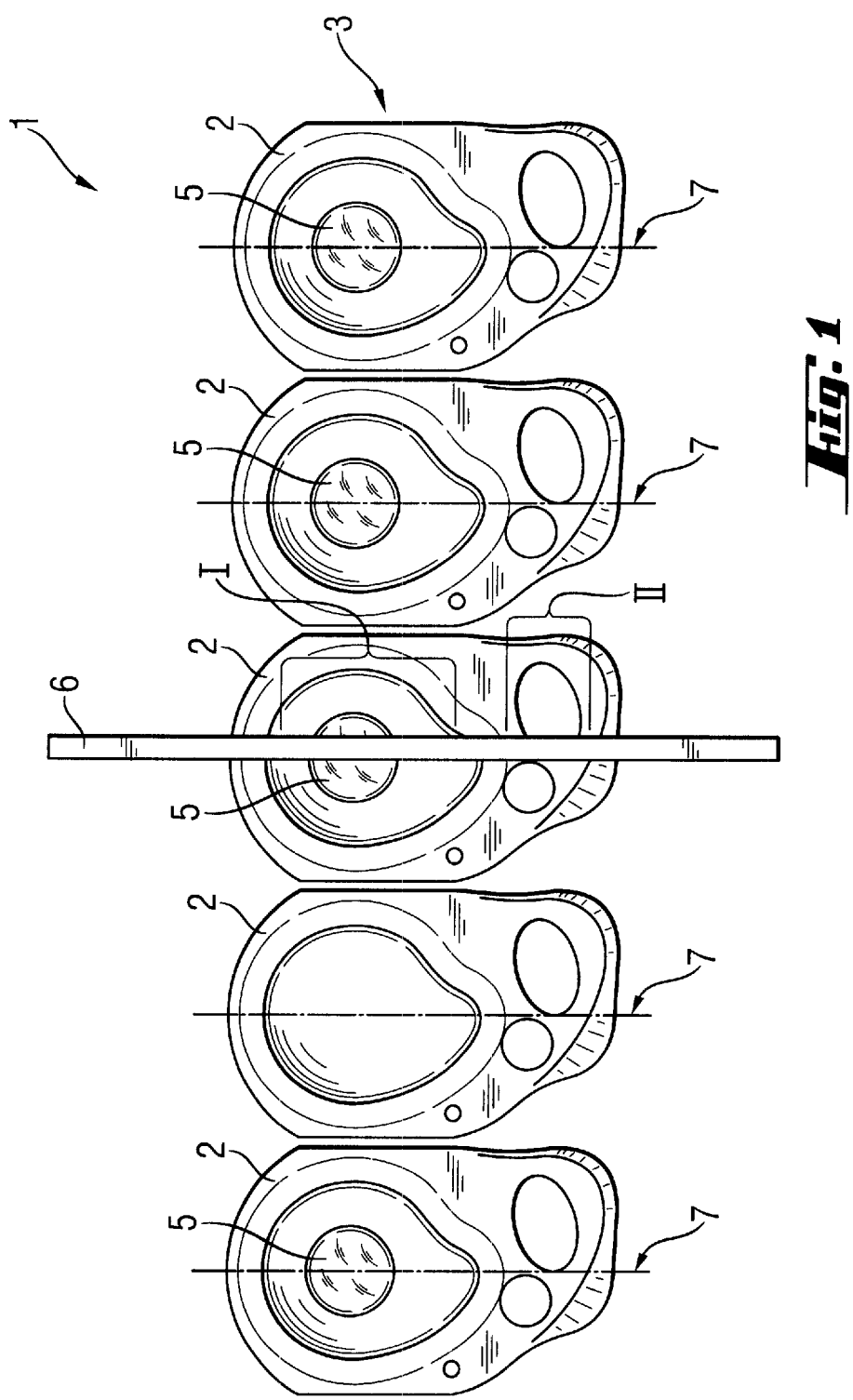

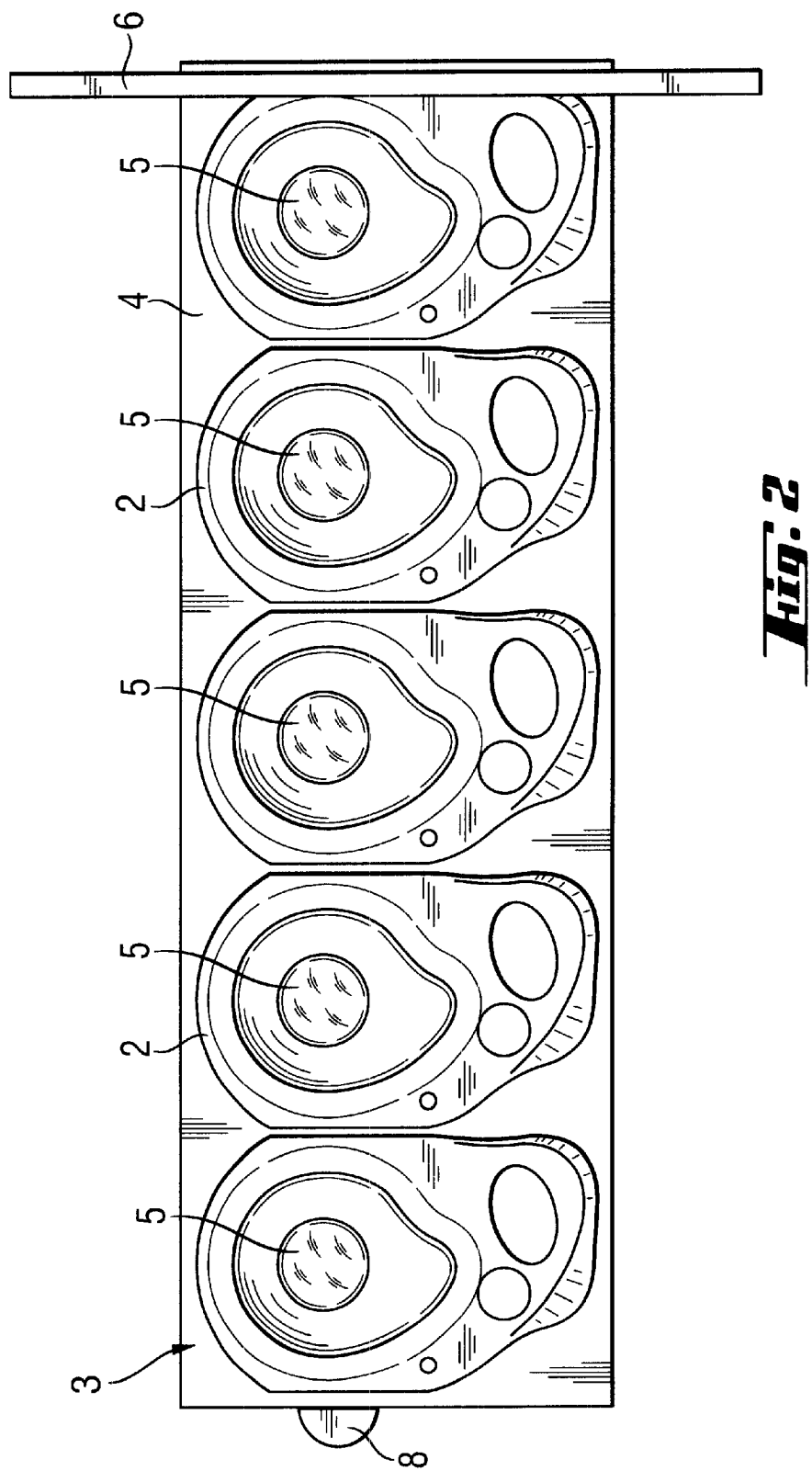

METHOD AND APPARATUS FOR DETECTING THE PRESENCE OF A MOULDING IN AN OPEN BLISTER PACKAGE BASED ON SENSED TEMPERATURE DIFFERENCES

BACKGROUND OF THE INVENTION

The invention relates to a method and apparatus for registering the presence of a moulding consisting of a biocompatible polymeric material, especially an ophthalmic lens, particularly a contact lens, in a package.

Mouldings consisting of a biocompatible polymeric material are usually placed in a package for storage and for transport. The packages in question are frequently so-called blister packages. A blister package consists of a plastic container, for example of polypropylene (PP), the top of which is sealed with film after the moulding has been placed in the plastic container.

In particular, contact lenses that are produced in large unit numbers, for example disposable contact lenses, are sealed into blister packages. Such contact lenses are preferably manufactured by the so-called mould or full-mould process. In this process, the lenses are manufactured into their final shape between two moulds, so that there is no need to subsequently finish the surfaces of the lenses, nor to finish the edges. Mould processes are described for example in PCT application no. WO/87/04390 or in European patent application EP-A-0 367 513.

To manufacture a contact lens, first of all a certain amount of the flowable starting material is placed in the female mould half. Afterwards, the mould is closed by placing the male mould half thereon. Normally, a surplus of starting material is used, so that, when the mould is closed, the excess amount is expelled into an overflow area adjacent to the outer mould cavity. The subsequent polymerisation or crosslinking of the starting material takes place by radiation with UV light, or by heat action, or by another non-thermal method.

The contact lenses produced in this manner are moulded parts having little mechanical stability and a water content of more than 60% by weight. After manufacture, the lens is metrologically checked, then packaged and subjected to heat sterilisation at 121° C. in an autoclave.

In U.S. Pat. No. 5,508,317, a new contact lens material is described, which is an important improvement in the chemistry of polymerisable starting materials for the manufacture of contact lenses. The patent discloses a water-soluble composition of a prepolymer, which is filled into the mould cavity and then crosslinked photochemically. Since the prepolymer has several crosslinkable groups, crosslinking is of particularly high quality, so that a finished lens of optical quality can be produced within a few seconds, without the necessity for subsequent extraction or finishing steps. Owing to the improved chemistry of the starting material as illustrated in the patent, contact lenses can be produced at considerably lower cost, so that in this way it is possible to produce disposable lenses.

Optical components produced in series, e.g. contact lenses, have to be checked for faults such as scratches, shrinkage or edges that have broken away. The components recognised as faulty are then rejected. However, at the moment there is no provision for checking whether a package has actually been filled with a contact lens. Under certain circumstances, empty packages may appear, which are not noticed. The client then discovers the empty package and is of course annoyed. However, if empty packages are recognised by chance or by spot checks, then either the whole batch has to be rejected or all the contact lens packages have to undergo 100% manual checking. Both procedures involve substantial costs.

The invention is therefore based on the problem of providing a testing method with which it is possible to detect, at low cost, whether a moulding, especially a contact lens, is actually present in the package.

BRIEF SUMMARY OF THE INVENTION

The invention solves this problem with the features indicated in claim 1. As far as further essential refinements are concerned, reference is made to the dependent claims.

By measuring the temperature of a package, it is possible to establish the presence of mouldings in a package. Packages containing a moulding, especially a contact lens, have a characteristic change in their temperature compared with a package without a contact lens. By evaluating the temperature difference, it is possible to determine whether or not there is a contact lens in a package. In particular, by using the detecting method according to the invention, one can determine whether there is a contact lens in the package directly after the filling procedure. Further details and advantages of the invention may be seen from the description that follows and the drawing. In the drawing,

BRIEF DESCRIPTION OF THE DRAWINGS

FIG. 1 shows a schematic illustration of an embodiment of a checking device according to the invention;

FIG. 2 shows a schematic illustration of a tool holder filled with packages.

DETAILED DESCRIPTION OF THE PREFERRED EMBODIMENTS

In FIG. 1, a checking device 1 according to the invention is illustrated. The checking device 1 is preferably integrated into a packaging appliance, not illustrated here, in such a way that it is possible to detect the presence of a contact lens 5 in the package during the production process. FIG. 1 shows a schematic illustration of five blister containers 2, arranged in series, of a packaging unit especially for contact lenses 5, which are transported continuously by the appliance on a tool holder 4 illustrated schematically in FIG. 2. Five blister containers 2 arranged in series form one blister strip 3. The blister containers 2 are joined together by a film strip not illustrated here, the outline of which corresponds to the contour of the top of the blister containers 2, since when the object to be packaged, preferably a contact lens 5, has been inserted, the film strip is heat-sealed to each blister container 2 individually. Prior to sealing the film, however, there is a provision according to the invention for checking whether each of the blister containers 2 contains a contact lens 5.

The checking device 1 comprises an infrared line camera 6 with a line resolution of preferably 128 pixels. It is preferably a camera made by Dias GmbH. The camera 6 advantageously has a sensitivity range of 0°–80° C. with a resolution of 0.5–0.1 K, preferably 0.2 K. However, other IR sensors may also be used. Measurement is based on the effect that the contact lens 5 automatically cools through evaporation of the moisture adhering to the contact lens. If the contact lens 5 is placed in the package, this package is colder than one which does not contain a contact lens. This effect is detectable by a local temperature measurement.

The camera 6 is preferably incorporated in the packaging appliance over the tool holders 4 which are arranged in series advantageously in five production lines 7 and can be conveyed on conveyor belts, so that the measuring range covers all five lines 7, not illustrated here. Of course, it may be possible to modify the number of conveyor belts and thus the production lines 7 in the packaging appliance. The repeat rate of the measurements in respect of a blister container is advantageously very high, so that the camera 6 is preferably in continuous operation. In this way, a high degree of certainty can be achieved in respect of the measurement results. The camera 6 is advantageously equipped with an integrated electronic evaluation means and all five production lines 7 can therefore be monitored in real time by the camera 6. Through an intersection point directly on the camera 6, the latter can be connected to the machine control of the packaging appliance. However, it is also conceivable for the evaluation signals from the camera to be passed directly to a PC control unit of the appliance. The software for control and evaluation of the camera allows a measuring line from the camera 6 to be subdivided into several zones that can be monitored separately. One zone division was advantageously undertaken in such a way that each production line 7 can be detected separately. In addition, advantageously each production line is again divided into two zones, whereby one of the two zones detects an area I of the blister container 2 with a contact lens 5 and the other zone detects an area II without a contact lens. These two zones are suitably separated from one another by a transition area in which measurements are not made. This is possible, since, in addition to the actual area where the contact lens 5 is received, the blister containers 2 have a relatively elongated gripping area.

The results of measurement from both zones are then compared. In this way, a relative measurement is made, so that the system is relatively independent of external influences, such as room temperature. If the difference of the temperature measurement between the zone with the contact lens and the zone without the contact lens 5 gives a value of less than 1, this means that a contact lens is present in the package. A starting signal can be set at a certain value, which is sent to a metering element or to the machine control. This enables a counting of the contact lenses 5 for example.

As is also evident from FIG. 2, the packaging appliance was advantageously equipped with a sensor 8, which detects when a tool holder 4 mounted with the blister containers 3 reaches the measuring area. The sensor 8 records when a tool holder 4 leaves and/or enters the measuring area. The sensor 8 may be designed for example as a light barrier; however, sensors operating capacitively or inductively are also possible. If the tool holder 4 has for example five blister containers, each holding one contact lens 5, then five contact lenses 5 must be detected. Since the results of measurement are passed directly to the machine control means, by making a comparison it can be established whether in fact five contact lenses 5 have been counted. Thus, it is not necessary to incorporate series of stoppers or other synchronisation measures. Of course it is also possible to design the checking system independently of a strip consisting of five blister packages, and to undertake individual detection and recordal.

The measuring process according to the invention is not an imaging process, since no image is made of the moulding to be examined. Instead, what is detected is a local temperature measurement.

In addition, ventilators not illustrated here are advantageously arranged over the five production lines between the lens deposit station and the IR camera. These enable the air exchange to be higher. In this way, the evaporation of water on the contact lenses is increased, so that there is increased cooling of the contact lenses. This leads to an improved signal-noise ratio.

Moreover, there may advantageously be a provision for the container detected as being empty to be automatically removed from the packaging appliance. The following tests carried out by way of example were effected using a detection set-up according to FIG. 1:

Test 1: Production of empty packages randomly distributed.

Approximately 50% empty packages were produced. These had not yet been filled with preserving solution. The empty packages were randomly distributed among the tool holders. An evaluation was made by making a comparison between a manual inspection and the results of the contact lenses detected by the IR camera.

Test Results:

|  | IR camera | manual inspection | consistency |
| --- | --- | --- | --- |
| CL present | 240 | 240 |  |
| CL not present | 180 | 180 |  |
| total | 420 | 420 | 420 100% |

The test shows that the presence of contact lenses is detected at a rate of 100% by the IR camera. There was not a single case in which the camera had not noticed the absence of a lens. The IR camera thus enables fault-free detection to be made of contact lenses in a package.

Test 2: Empty packages with the addition of a defined amount of water

In this test, all packs contained no contact lenses. In addition, a defined amount of water was added to one of the containers in a series of five. The amount of water was 50 μl for the first 50 tool holders and 100 μl for the last 34 tool holders. The aim of this test was to investigate the influence of possible water spillages on the results of measurement. An evaluation was again made by making a comparison between a manual inspection and the results of the contact lenses detected by the IR camera.

Test Results:

|  | IR camera | manual inspection | consistency |
| --- | --- | --- | --- |
| CL present | 0 | 0 |  |
| CL not present | 420 | 420 |  |
| total | 420 | 420 | 420 100% |

The test shows that the detection system also operates in a trouble-free manner after the addition of water and accurately detects the absence of contact lenses.

In all, the invention offers the possibility of checking in a simple manner the presence of mouldings, especially ophthalmic lenses, particularly contact lenses, in a package which can be either open or closed and contains no preserving solution. Owing to the high repeat rate of measurements, the camera can be operated continuously.

I claim:

1. A method for detecting the presence of a moulding in an open blister package, the method comprising:

measuring at least one temperature of a first open blister package with a moulding to obtain a first temperature measurement;

measuring at least one temperature of a second open blister package without a moulding to obtain a second temperature measurement; and detecting the presence of the moulding in the first open blister package based on a difference between the first temperature measurement and the second temperature measurement.

2. The method according to claim 1, wherein the first and second temperature measurements are local temperature measurements.

3. The method according to claim 1, wherein an infrared line camera is used to measure the temperatures of the open blister packages.

4. The method according to claim 3, wherein said infrared line camera has a resolution of 0.5 to 0.1 K.

5. The method according to claim 4, wherein said infrared line camera has a resolution of 0.2 K.

6. The method according to claim 3, wherein a sensor is used to detect when a package enters and/or leaves a measuring area of the infrared line camera.

7. The method according to claim 1, wherein temperatures of several open blister packages are measured simultaneously.

8. The method according to claim 1, wherein ventilators are arranged over the package to increase air exchange over the package prior to measuring the temperatures.

9. The method according to claim 1, wherein the moulding is a contact lens.

10. A method for detecting the presence of a moulding in an open blister package, the method comprising:

measuring a first local temperature distribution of a first zone of an open blister package, wherein the moulding is contained in the first zone;

measuring a second local temperature distribution of a second zone of the open blister package, wherein the moulding is not contained in the second zone; and detecting the presence of the moulding in the open blister package based on a difference between the first local temperature distribution of the first zone and the second local temperature distribution of the second zone.

11. The method according to claim 10, wherein local temperature measurements of several open blister packages are carried out simultaneously.

12. The method according to claim 10, wherein an infrared line camera is used to measure local temperature distributions of the open blister packages.

13. The method according to claim 12, wherein said infrared line camera has a resolution of 0.5 to 0.1 K.

14. The method according to claim 13, wherein said infrared line camera has a resolution of 0.2 K.

15. The method of claim 12, wherein a sensor is used to detect when a package enters and/or leaves a measuring area of the infrared line camera.

16. The method of claim 10, wherein ventilators are arranged over the open blister package to increase air exchange over the open blister package prior to measuring the local temperature distributions.

17. A method of claim 10, wherein the moulding is a contact lens.

18. An apparatus for detecting the presence of a moulding in an open blister package, comprising:

an infrared line camera for measuring local temperature distributions of at least two zones of the open blister package, wherein the moulding is contained in one of the at least two zones of the open blister package while the moulding is not contained in the other zone of the open blister package;

a sensor for detecting when the open blister package enters and/or leaves a measuring area of the infrared line camera; and an electronic evaluation means for evaluating a difference between the local temperature distributions of the at least two zones of the open blister package.

19. An apparatus according to claim 18, wherein the infrared line camera has a resolution of 0.5 to 0.1 K.

20. An apparatus according to claim 19, wherein the infrared line camera has a resolution of 0.2 K.

* * * * *